Figure 1:
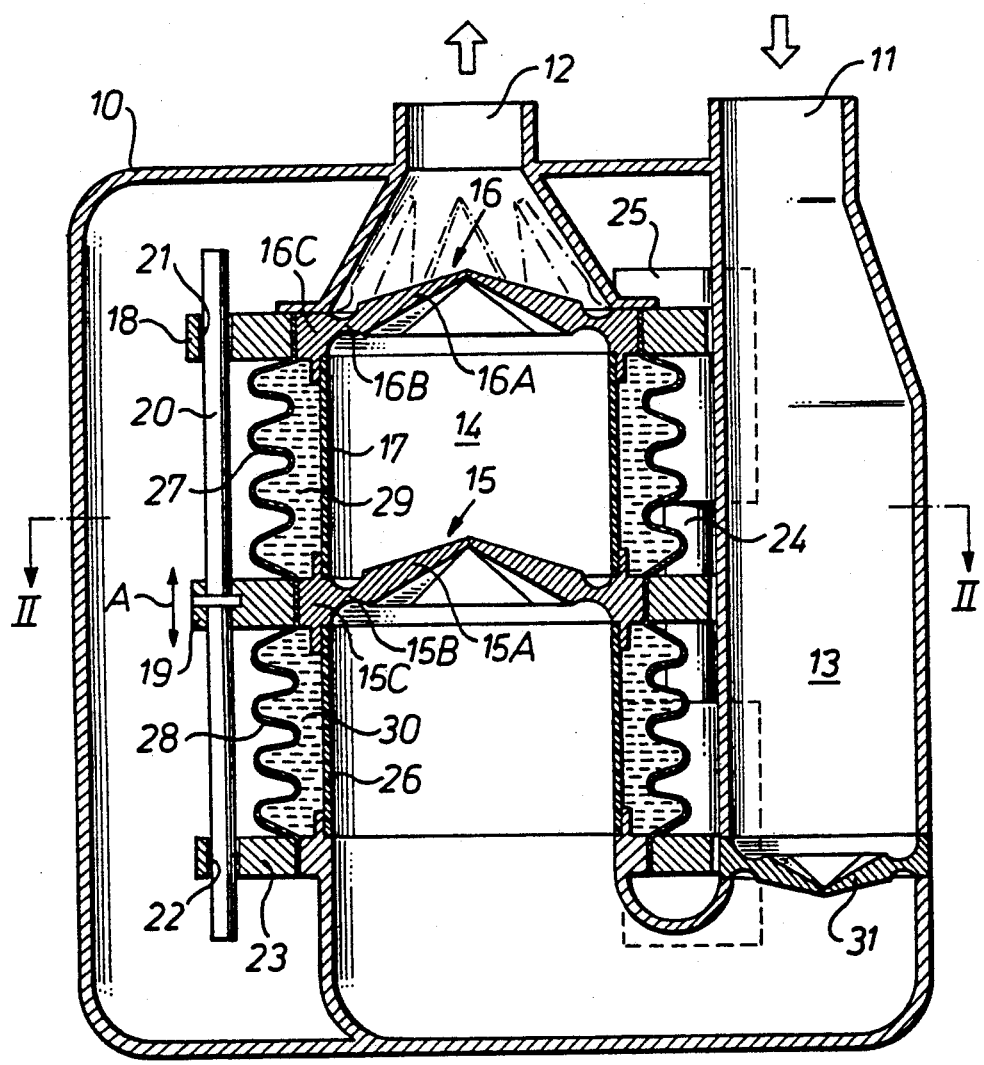

United States Patent [19]
Biro et al.

[11] Patent Number: 5,108,426
[45] Date of Patent: Apr. 28, 1992

[54] IMPLANTABLE BLOOD PUMP

[75] Inventors: Jan C. Biro, Karlapan 5, S-114 60 Stockholm; Gunther G. Nabholz, Saltsjo-Boo, both of Sweden

[73] Assignee: Jan Charles Biro, Stockholm, Sweden

[21] Appl. No.: 550,825

[22] Filed: Jul. 10, 1990

[51] Int. Cl.⁵ .............................. A61M 1/12
[52] U.S. Cl. ........................ 623/3; 417/472; 417/545
[58] Field of Search ............ 604/7, 33, 151, 153; 623/3; 417/412, 413, 472, 473, 540, 545, 550, 551

[56] References Cited

U.S. PATENT DOCUMENTS

| | | | |
|---|---|---|---|
| 3,106,204 | 10/1963 | Paramelle | 417/473 |
| 3,127,846 | 4/1964 | Kerns | 417/412 |
| 3,974,825 | 8/1976 | Normann | 623/3 X |
| 4,131,604 | 12/1978 | Szycher | 623/3 X |
| 4,750,868 | 6/1988 | Lunback | 417/412 X |
| 4,781,716 | 11/1988 | Richelsoph | 623/3 |
| 4,925,377 | 5/1990 | Inacio et al. | 417/472 |

FOREIGN PATENT DOCUMENTS

| | | | |
|---|---|---|---|
| 0156781 | 10/1985 | European Pat. Off. | |
| 3810660 | 10/1988 | Fed. Rep. of Germany | 623/3 |
| 1504359 | 8/1989 | U.S.S.R. | 417/473 |

Primary Examiner—Robert A. Hafer
Assistant Examiner—Sam Rimell
Attorney, Agent, or Firm—Fleit, Jacobson, Cohn, Price, Holman & Stern

[57] ABSTRACT

An implantable blood pump comprises a flow passage (13) and two valves (15, 16), located spaced apart in the longitudinal direction of said passage (13) and permitting a flow of blood therethrough only in one direction and defining a pump chamber (14) therebetween, having an elastically deformable peripheral wall (17). The valve located at the inlet end of the pump chamber (14) being supported by a holder (19), arranged for reciprocating movement in the longitudinal direction of the pump chamber (14) by means of periodically operating driving means (24, 25). In order to reduce the risk of thrombosis within the pump chamber (14), said wall is formed by an elastically extensible hose (17), surrounded by a bellows (27), defining a liquid-filled annular space (29) around said hose (17) and being sealingly connected thereto at opposite ends thereof.

7 Claims, 2 Drawing Sheets

IMPLANTABLE BLOOD PUMP

The present invention relates to an implantable blood pump.

More particularly, the invention relates to such a blood pump of the kind, comprising a flow passage, extending from an inlet of the pump to an outlet thereof and containing two valves, located spaced apart in the longitudinal direction of said flow passage and arranged each to permit a blood flow to pass it only in direction from the pump inlet and towards the pump outlet, said two valves defining therebetween a pump chamber having an elastically deformable peripheral wall, at least along a portion of its length, the valve located at the inlet end of the pump chamber being supported for limited reciprocating movement in the longitudinal direction of the pump chamber by means of a correspondingly movable valve holder, connected to periodically operating force-generating means, arranged to cause an alternating compression and expansion of the pump chamber through an alternating movement of said valve in direction towards and away from the valve located at the outlet end of the pump chamber during simultaneous elastic deformation of said wall of the pump chamber.

A blood pump of said kind is previously known through EP-A2 0 156 781 which discloses a pump where said elastically deformable peripheral wall of the pump chamber has a strongly bulged shape, hereby constantly forming an outward bulge of large diameter between the two ends of the pump chamber. As a consequence, in the portion of the pump chamber located closest to the outer peripheral portion of said bulge, there exists a zone where the blood flow is strongly reduced and hence, the risk of thrombosis is very high.

The invention has for its object to provide an improved implantable blood pump of the kind initially specified, which makes it possible to avoid the abovementioned very serious disadvantage of the prior pump.

According to the invention, for this purpose, there is proposed an implantable blood pump of said kind, primarily characterized in that said elastically deformable peripheral wall of the pump chamber is formed by an elastically extensible flexible hose, which is surrounded by a bellows, sealingly connected to said hose at opposite ends thereof and defining a liquid-filled annular space around said hose.

The invention makes it possible to eliminate the prior need for an outward bulge of large diameter on the elastically deformable peripheral wall of the pump chamber. In the pump according to the invention, the elastically extensible hose forming said wall of the pump chamber may instead have an approximately constant or, in any case, only modestly varying diameter along its length. Hereby, the invention eliminates the risk of thrombosis while simultaneously offering the additional advantage of reducing the flow resistance in the pump chamber by making the flow therethrough less turbulent.

A primary object of the bellows and the annular liquid-filled space around the hose defined by the bellows is to prevent the internal positive pressure produced within the hose during the compression phase of the pump chamber from causing an elastic radial expansion of the hose and a consequent unfavourable reduction of the pumping action. However, the bellows and the liquid-filled annular space not only serve to provide a protection against an undesirable reduction of the pumping action but also to cause an additional contribution to the pumping action following from the successive decrease of the length of the hose during the compression phase of the pump chamber. This additional contribution to the pumping action is caused by an increase of the pressure in the liquid-filled space occurring during said phase and giving reason to a radial compression of the hose.

The abovementioned movability of the valve located at the inlet end of the pump chamber and of the holder for said valve requires a corresponding movability of the adjacent portion of the flow passage. In a preferred embodiment of the invention, for this purpose, a portion of the flow passage located adjacent to and on the upstream side of the pump chamber has an elastically deformable peripheral wall, formed by another elastically extensible flexible hose, which is surrounded by another bellows, sealingly connected to said another hose at opposite ends thereof and defining another liquid-filled annular space around said another hose. In a pump according to this embodiment, two identical hoses and two identical bellows may be used.

The liquid filling the annular space around the hose or each hose, respectively, may preferably consist of a physiological sodium chloride solution or another physiological solution. In the case of any leakage of fluid from the annular space to the flow passage extending through the hose, such a solution will not have any traumatic effect. In this connection, it also serves to be mentioned that any rupture in the hose containing the pump chamber or any leakage past the edges of said hose need not have any fatal consequences since the bellows surrounding said hose will permit the pump to continue operating, although with a reduced pumping effect.

It may be desirable to prevent pulsations in the pressure existing in the inlet of the pump. In order to prevent the reciprocating movement of the valve located at the inlet end of the pump chamber from causing such pressure pulsations, the flow passage may contain a third valve, arranged to permit a blood flow to pass it only in direction from the pump inlet and towards the pump outlet, said third valve being located on the upstream side of the pump chamber and spaced therefrom in the longitudinal direction of said flow passage.

The force-generating means may be of many different types. However, in order to facilitate a convenient use of the pump as an implantable blood pump, said means may preferably comprise electric or electromagnetic driving means for said movable valve holder, mounted within an outer housing of the pump.

The valves provided in the flow passage may be constructed in many different ways. However, each one of said valves may suitably comprise a generally disklike member of at least slightly conical or domed shape, having its smallest end turned towards the pump outlet, a central portion of said member being provided with a plurality of radially extending slots, dividing it into a plurality of generally triangular resiliently flexible flaps, having adjacent apices. These flaps may preferably be provided with perpheral base portions of reduced thickness in order hereby to facilitate flexure of the flaps.

Figure 2:
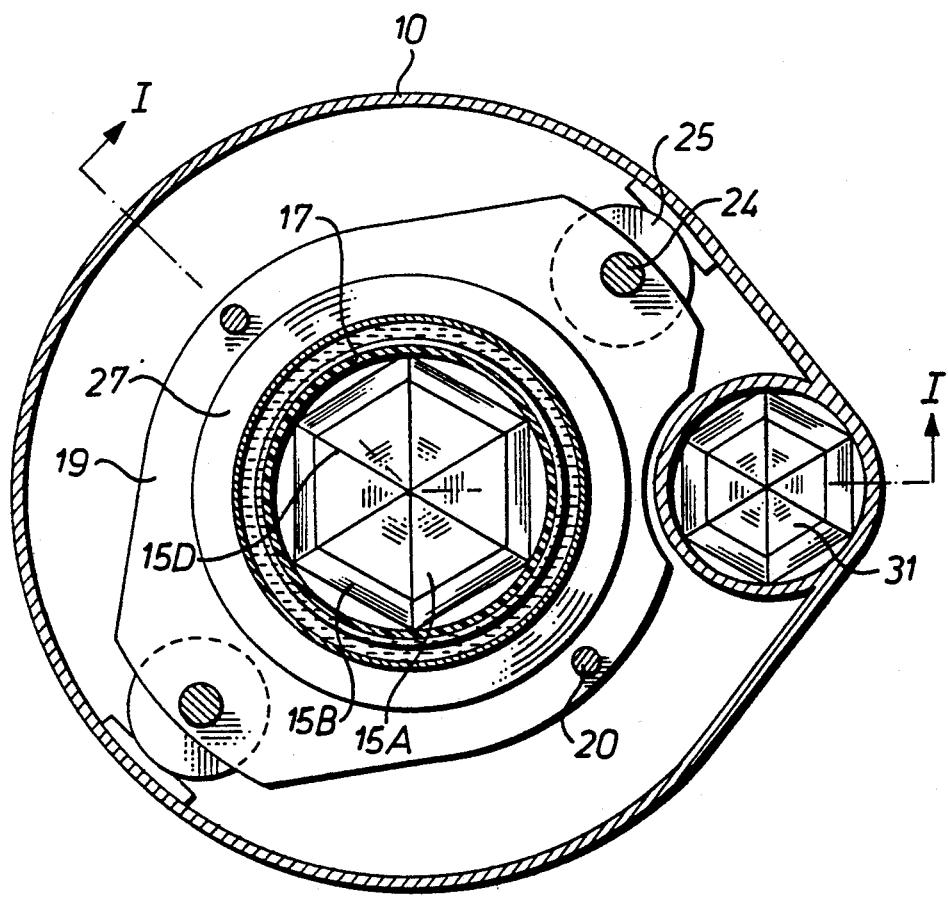

Below, the invention will be further described by way of example with reference to the accompanying diagrammatic drawings, in which:

FIG. 1 shows a side elevation view of an implantable blood pump according to an embodiment of the invention, in section taken along line I—I in FIG. 2, and FIG. 2 shows a top plan view of said pump, in section taken along line II—II in FIG. 1.

The blood pump shown in the drawings comprises a housing 10, provided with an inlet 11 and an outlet 12, both formed by short pipes protruding from housing 10. A generally U-shaped blood flow passage 13 extends between inlet 11 and outlet 12 within said housing. In the illustrated embodiment, the leg of said flow passage, connected to outlet 12, has a larger cross-sectional area than the leg connected to inlet 11.

The upper portion of the wider leg of passage 13, connected to outlet 12, forms a pump chamber 14, defined between two valves, generally designated 15 and 16 and which are located in spaced apart relationship in said leg of passage 13. Valve 15 is located at the inlet end of pump chamber 14, while valve 16 is located at the outlet end of said chamber. Each valve 15 and 16, respectively, acts as a check valve, permitting a blood flow to pass it only in direction from inlet 11 and towards outlet 12.

In order to exhibit such a function, each valve 15 and 16, respectively, is formed by a disk-like member of elastomeric material and of slightly conical shape, having its smallest end turned towards outlet 12, i.e. in an upward direction according to FIG. 1, and provided with a plurality of radial slots, dividing a central portion of said member into a corresponding plurality of generally triangular resiliently flexible flaps 15A and 16A, respectively, the pieces of which are located adjacent to each other at the centre of said member. Each one of these flaps is connected to an annular continuous radially outer portion 15C and 16C, respectively, of the valve by means of a peripheral base portion 15B and 16B, respectively, having a reduced thickness. In FIG. 2, the abovementioned slots in valve 15 have been designated 15D.

Flaps 15A and 16A of valves 15 and 16, respectively, will assume their closed positions shown in FIG. 1 as long as the pressure acting on the downstream side of the valve in question is higher than the pressure acting on the upstream side thereof. However, as soon as the pressure on the upstream side of any of said valves becomes slightly higher than the pressure on the downstream side thereof, the flaps of this valve will be swung in an upward direction towards fully open positions, indicated in dash-dotted lines for flaps 16A in FIG. 1, under simultaneous separation of their apices. This opening movement of the flaps takes place substantially as a resilient flexure in the thinned base portions of the flaps.

Between the two valves 15 and 16, pump chamber 14 has an elastically deformable peripheral wall, formed by an elastically extensible hose 17 which may consist of any suitable elastomeric material. This hose extends between the two valves 15 and 16 and has its ends sealingly connected to the radially outer annular portion 15C and 16C, respectively, of said valves.

The upper valve 16, which is located at the outlet end of pump chamber 14, is mounted in a holder 18, secured in a stationary position within housing 10 and having the shape of a plane plate. The lower valve 15, which is located at the inlet end of pump chamber 14, is mounted in a plane plate-like holder 19, mounted for limited reciprocating movement in a vertical direction within housing 10, i.e. for movement in a direction parallel to the longitudinal direction of pump chamber 14. At two diametrically opposite portions thereof, valve holder 19 is rigidly connected to two vertical guide rods 20 which are displaceably lodged in individual bores 21 in holder 18 and in individual bores 22 in a stationary plate member 23, located below holder 19. At two other diametrically opposite portions thereof, holder 19 is rigidly connected to two vertical rods 24, forming armatures of two electromagnetic driving units, each comprising two solenoids 25 which are mounted in stationary positions within housing 10 and into which the appurtenant rod 24 extends with opposite end portions thereof.

Also the portion of passage 13 located immediately below valve 15 comprises an elastically deformable peripheral wall. This wall is formed by another elastically extensible flexible hose 26, which is quite similar to hose 17 and which has its upper end sealingly connected to valve 15, while the lower end thereof is sealingly connected to a stationary wall portion of passage 16, received in an opening in member 23.

The two hoses 17 and 26 are surrounded by axially extensible and compressible bellows 27 and 28, respectively, defining a closed annular space 29 and 30, respectively, around each hose 17 and 26. Each annular space 29 and 30, respectively, is wholly filled with a liquid, preferably consisting of a physiological sodium chloride solution.

In the lower portion of the narrow leg of passage 13, connected to inlet 11, a third valve 31 is mounted. This valve is constructed in the same manner as valves 15 and 16 and, similar to those, it acts as a check valve, permitting a blood flow to pass it only in direction from inlet 11 and towards outlet 12.

The manner of operation of the pump will now be described. By means of the two electromagnetic driving units, holder 19 and valve 15 may be brought to carry out a reciprocating movement in a vertical direction as indicated by arrow A in FIG. 1. Hereby, an alternating compression and expansion of pump chamber 14 may be effected. During the upward working stroke, valve 15 will remain closed due to the pressure increase occurring in pump chamber 14. However, said pressure increase will bring valve 16 to open and hereby cause an outflow of blood from pump chamber 14 towards outlet 12. Simultaneously, the volume of the portion of passages 13 located between valves 16 and 31 is increased, whereby a blood flow will pass into said portion of passage 13 through valve 31.

During the abovementioned working stroke of valve 15, bellows 27 is subjected to a compression in its longitudinal direction. Hereby, the liquid contained in annular space 29 will cause an increased compression of pump chamber 14 as it will bring the walls of hose 17 to become deflected in a radial inward direction in order to maintain the volume of space 29 substantially constant.

When, by means of the electromagnetic driving units, valve 15 is then brought to make a return stroke, during which it will move in a downward direction from valve 16 and hereby cause an expansion of pump chamber 14, valve 16 will be closed, while valve 15 will become opened and permit pump chamber 14 to be refilled with blood from the portion of passage 13 located on the upstream side of valve 15. Bellows 27 is simultaneously extended in its longitudinal direction and so is the liquid-filled space 29. Hereby, hose 17 is subjected to an outer negative pressure causing it to expand in a radial outward direction and thereby to increase the expansion of the pump chamber.

Hose 26 and bellows 28 cooperate in similar manner to provide an increased alternating expansion and compression of the portion of passage 13 located between valves 15 and 31.

The invention is not restricted to the embodiment above described and shown in the drawings. Instead, said embodiment may be modified in many different ways within the scope of the invention. Especially, it should be noted that the precise design and construction of the various components of the pump as well as the connections therebetween may be altered. In the illustrated embodiment, the connections between various components, such as between hoses 17, 26 and valves 15, 16 as well as between said valves and bellows 27, 28 and valve holders 18, 19 may be obtained by means of suitable adhesives. However, many other types of connections may also be used.

We claim:

1. An implantable blood pump, comprising a flow passage, extending from an inlet of the pump to an outlet thereof and containing two valves, located spaced apart in the longitudinal direction of said flow passage and arranged each to permit a blood flow to pass it only in direction from the pump inlet and towards the pump outlet, said two valves defining therebetween a pump chamber having an elastically deformable peripheral wall, at least along a portion of its length, the valve located at the inlet end of the pump chamber being supported for limited reciprocating movement in the longitudinal direction of the pump chamber by means of a correspondingly movable valve holder, connected to periodically operating force-generating means, arranged to cause an alternating compression and expansion of the pump chamber through an alternating movement of said valve in direction towards and away from the valve located at the outlet end of the pump chamber during simultaneous elastic deformation of said wall of the pump chamber, characterized in that said elastically deformable peripheral wall of the pump chamber is formed by an elastically extensible flexible hose, which is surrounded by a bellows, sealingly connected to said hose at opposite ends thereof and defining a liquid-filled annular space around said hose.

2. A blood pump according to claim 1, characterized in that a portion of the flow passage located adjacent to and on the upstream side of the pump chamber has elastically deformable peripheral wall, formed by another elastically extensible flexible hose, which is surrounded by another bellows, sealingly connected to said another hose at opposite ends thereof and defining another liquid-filled annular space around said another hose.

3. A blood pump according to claim 1, characterized in that said liquid consists of a physiological sodium chloride solution or another physiological solution.

4. A blood pump according to claim 1, characterized in that said flow passage contains a third valve, arranged to permit a blood flow to pass it only in direction from the pump inlet and towards the pump outlet, said third valve being located on the upstream side of the pump chamber and spaced therefrom in the longitudinal direction of said flow passage.

5. A blood pump according to claim 1, characterized in that said force-generating means comprise electric or electromagnetic driving means for said movable valve holder, mounted within an outer housing of the pump.

6. A blood pump according to claim 1, characterized in that each valve comprises a generally disk-like member of at least slightly conical or domed shape, having its smallest end turned towards the pump outlet, a central portion of said member being provided with a plurality of radially extending slots, dividing it into a plurality of generally triangular resiliently flexible flaps, having adjacent apices.

7. A blood pump according to claim 6, characterized in that said flaps are provided with peripheral base portions of reduced thickness.

* * * * *